United States Patent
Tehrani et al.

(10) Patent No.: US 7,870,782 B2
(45) Date of Patent: Jan. 18, 2011

(54) METHOD AND APPARATUS FOR DETERMINING THE PROPERTIES OF DRILLING FLUIDS

(75) Inventors: Mostafa Ahmadi Tehrani, Banchory (GB); Jacqueline Joan Cameron, Aberdeen (GB)

(73) Assignee: M-I L.L.C., Houston, TX (US)

( * ) Notice: Subject to any disclaimer, the term of this patent is extended or adjusted under 35 U.S.C. 154(b) by 442 days.

(21) Appl. No.: 12/049,953

(22) Filed: Mar. 17, 2008

(65) Prior Publication Data

US 2008/0236253 A1    Oct. 2, 2008

Related U.S. Application Data

(60) Provisional application No. 60/908,106, filed on Mar. 26, 2007.

(51) Int. Cl.
*E21B 49/02* (2006.01)
(52) U.S. Cl. .................................. 73/152.07
(58) Field of Classification Search ............ 73/38, 73/152.07, 152.09, 152.11
See application file for complete search history.

(56) References Cited

U.S. PATENT DOCUMENTS

| | | | | |
|---|---|---|---|---|
| 2,942,176 | A * | 6/1960 | Brownscombe et al. ...... 324/376 |
| 4,486,714 | A * | 12/1984 | Davis et al. .................. 324/376 |
| 4,506,542 | A * | 3/1985 | Rose .............................. 73/38 |
| 4,543,821 | A * | 10/1985 | Davis, Jr. ................. 73/152.07 |
| 4,748,849 | A | 6/1988 | Jamison et al. |
| 5,069,065 | A * | 12/1991 | Sprunt et al. ............. 73/152.09 |
| 5,105,656 | A * | 4/1992 | Jackson ...................... 73/61.63 |
| 5,209,104 | A * | 5/1993 | Collins et al. .................. 73/38 |
| 5,233,863 | A * | 8/1993 | Surjaatmadja et al. ..... 73/61.64 |
| 5,265,461 | A * | 11/1993 | Steiger et al. .................. 73/38 |
| 5,265,462 | A * | 11/1993 | Blauch et al. .................. 73/38 |
| 5,297,420 | A * | 3/1994 | Gilliland et al. ................ 73/38 |
| 5,309,761 | A * | 5/1994 | Ravi et al. ............... 73/152.21 |
| 5,325,723 | A * | 7/1994 | Meadows et al. ............. 73/794 |
| 5,493,226 | A * | 2/1996 | Honarpour et al. .......... 324/376 |
| 5,503,001 | A * | 4/1996 | Wong ............................. 73/38 |
| 5,987,969 | A | 11/1999 | Joseph et al. |
| 6,330,826 | B1 | 12/2001 | Meeten et al. |
| 6,543,276 | B2 * | 4/2003 | Murphy et al. ............ 73/61.63 |
| 6,584,833 | B1 | 7/2003 | Jamison et al. |
| 6,931,916 | B2 | 8/2005 | Zamora et al. |
| 7,472,588 | B2 * | 1/2009 | Slavin et al. ............. 73/152.11 |
| 2008/0257030 | A1 * | 10/2008 | Slavin et al. ............. 73/152.11 |

OTHER PUBLICATIONS

PCT International Search Report issued in PCT/US2008/058258 dated Jul. 21, 2008 (3 pages).
PCT Written Opinion PCT issued in PCT/US2008/058258 dated Jul. 21, 2008 (3 pages).

* cited by examiner

*Primary Examiner*—John Fitzgerald

(57) ABSTRACT

Methods and apparatus to measure flow of a drilling fluid composition include a test housing including a test matrix located between an inlet and an outlet, a test valve connected between the inlet of the test housing and a fluid reservoir, and a pressure assembly configured to apply pressure to drilling fluid contained in the fluid reservoir. The apparatus and methods further include a sample valve connected to the outlet of the test housing and a measurement device configured to measure a filtrate fluid flowing through the outlet. A method to measure flow of a drilling fluid includes measuring an amount of filtrate fluid flowing through the test matrix as a function of time.

25 Claims, 3 Drawing Sheets

METHOD AND APPARATUS FOR DETERMINING THE PROPERTIES OF DRILLING FLUIDS

CROSS-REFERENCE TO RELATED APPLICATIONS

This applications claims priority, pursuant to 35 U.S.C. 119(e) to U.S. Provisional Patent Application No. 60/908, 106, filed Mar. 26, 2007. That application is expressly incorporated by reference in its entirety.

BACKGROUND

1. Field of the Disclosure

The present disclosure generally relates to apparatus and methods to test drilling fluids. More particularly, the present disclosure relates to methods and apparatus to measure the loss of drilling fluids through selected formations over time. More particularly still, the present disclosure relates to apparatus and methods to test the effectiveness of loss prevention materials entrained in drilling fluids against selected formations.

2. Background Art

When drilling in depleted zones or otherwise weak formations, wellbore instability and formation damage are major concerns for operators. Because of the economic incentives to extract as much of the hydrocarbon deposits from subterranean reservoirs as possible, it is often necessary to drill in depleted zones and through weakened formations. However, drilling through such highly depleted zones may increase the risk of losing drilling fluid (i.e., drilling "mud") through fractures or other features of the formation. Therefore, it is advantageous to drill using a drilling fluid optimized for a particular formation such that the loss of drilling fluid is minimized.

As such, drilling fluids designed for depleted zones should be capable of maintaining or enhancing wellbore stability while simultaneously preventing severe drilling fluid matrix (i.e., the base fluid) losses by healing natural or induced fractures. In addition to preventing severe matrix losses, loss control may also reduce the risk of differential sticking. The rheology of the base drilling fluid plays a role in flow through porous media, particularly in the initial stages of contact between the fluid and the freshly drilled formation.

Fluid loss during this initial stage is referred to as "spurt loss" and may continue until an effective filtercake or bridge is built-up to act as a barrier to further losses. In high permeability formations, or where induced or natural fractures exist, whole drilling fluid may be lost into the formation during this stage which, if left uncontrolled, may continue and lead to severe mud losses and loss of the ability to control the well.

However, most of these problems may be averted (or their effect minimized) by the inclusion of an effective loss prevention material ("LPM") in the drilling fluid mixture. However, because formations and wellbores are unique, no single LPM configuration (e.g., material, size, concentration, etc.) will be optimal for all drilling conditions. Therefore, it would be highly desirable to develop methods and apparatus to experimentally test varying drilling fluid and LPM compositions on a variety of formation structures.

Formerly, a permeability plugging test ("PPT") was performed to measure matrix fluid loss characteristics. In a PPT, matrix loss characteristics were evaluated on relatively thin ceramic discs having large pore throat sizes. As such, the flow path through the ceramic media was relatively short and generally did not allow the mud rheology sufficient time to exert control over the loss of the fluid matrix.

Therefore, a better alternative to the PPT would be highly desired. Such an alternative would involve a matrix loss test over a relatively longer test medium such that the ability of a drilling fluid's LPM to control loss beyond the "spurt loss" stage could be measured. Such an alternative would provide a flow path of adequate length so that the fluid rheology may build matrix loss resistance through gelling or the filtercake formation.

SUMMARY OF THE CLAIMED SUBJECT MATTER

In one aspect, embodiments of the present disclosure include an apparatus to measure flow of a drilling fluid composition. The apparatus includes a test housing including a test matrix located between an inlet and an outlet, a test valve connected between the inlet of the test housing and a fluid reservoir, and a pressure assembly configured to apply pressure to drilling fluid contained in the fluid reservoir. The apparatus further includes a sample valve connected to the outlet of the test housing and a measurement device configured to measure a filtrate fluid flowing through the outlet.

In another aspect, embodiments of the present disclosure include a method to measure flow of a drilling fluid. The method includes locating a test matrix in a test housing wherein the test housing includes an inlet in communication with a test valve and an outlet in communication with a sample valve. The method further includes selectively communicating a fluid reservoir with the test housing through the test valve and pressurizing drilling fluid in the fluid reservoir with a pressure assembly. The method further includes opening the sample valve, opening the test valve, and measuring an amount of filtrate fluid flowing through the test matrix as a function of time.

Other aspects and advantages of the disclosure will be apparent from the following description and the appended claims.

DETAILED DESCRIPTION

The present disclosure relates to methods and apparatus to evaluate matrix loss characteristics of drilling fluids under a variety of differential pressures. Selected embodiments include forcing a known volume of a drilling fluid through a porous medium of known permeability or mean pore size, by applying a known differential pressure across the matrix. A flow versus time profile of the fluid exiting the porous medium may be used to determine matrix loss characteristics of the drilling fluid composition being tested.

Figure 1:
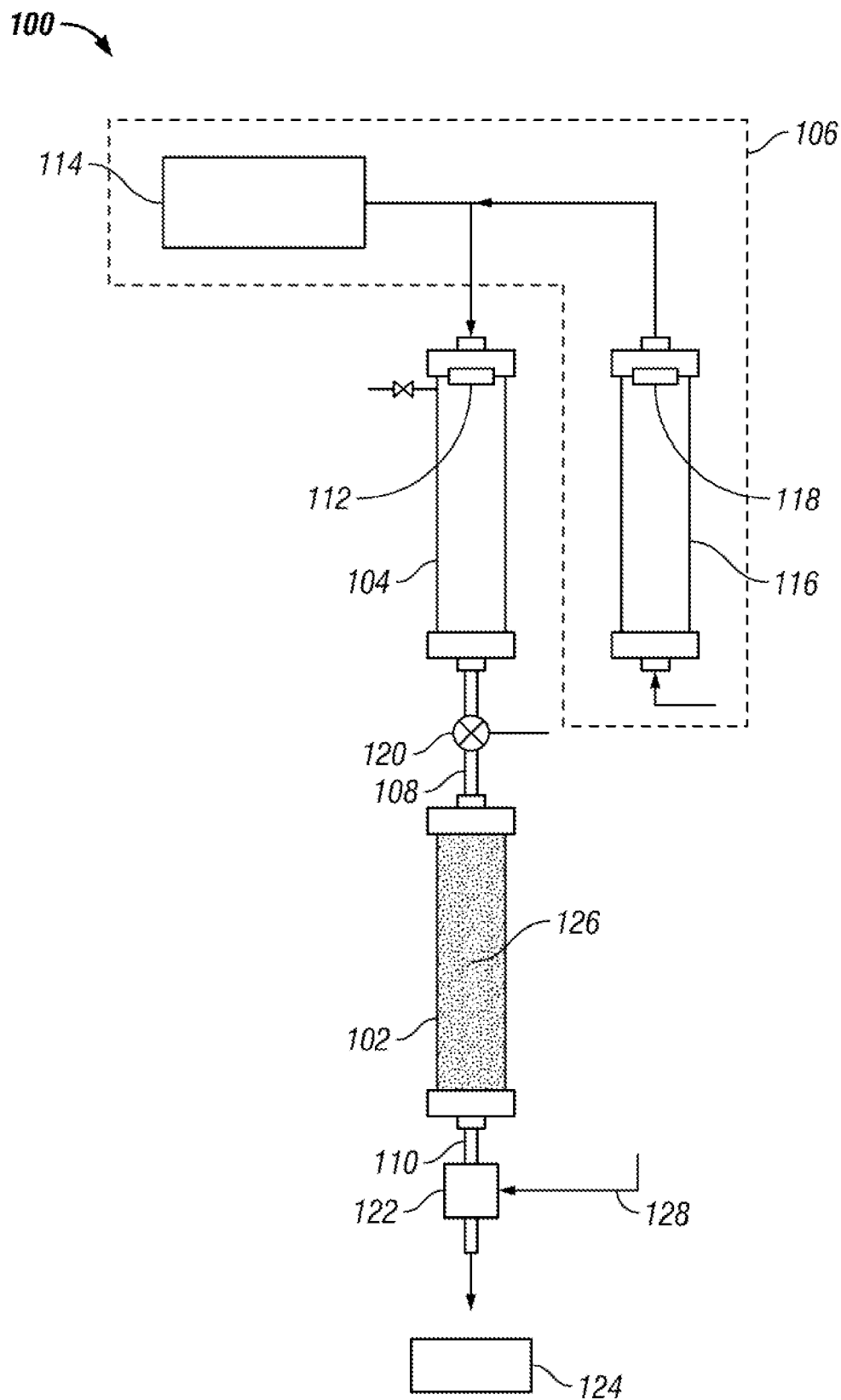
FIG. 1 is a schematic representation of an assembly to measure matrix loss of a particular drilling fluid in accordance with embodiments of the present disclosure.

Referring initially to FIG. 1, an apparatus 100 to measure loss of a drilling fluid composition is shown schematically. As shown, measurement apparatus 100 includes a test housing 102, a fluid reservoir 104, and a pressure assembly 106. Test housing 102 is shown as a double-ended, high-temperature, high-pressure ("HTHP") vessel having an inlet 108 at its upper end and an outlet 110 at its lower end. While test housing 102 is shown as a cylinder having an approximate 500 ml capacity, it should be understood by one of ordinary skill in the art that various other configurations and geometries (e.g., a spherical vessel) may be used without departing from the scope of the claims appended hereto. Furthermore, as an HTHP vessel, test housing 102 should be capable of sustaining elevated internal pressures (e.g., up to 10,000 psi) and temperatures (e.g., over 200° C.) in excess of those expected to be experienced during testing conditions. However, in embodiments, test housing 102 may not be required for high-temperature service.

Furthermore, as shown, fluid reservoir 104 is constructed as a pressure accumulator containing a known volume of the drilling fluid composition to be tested. As such, a working fluid from pressure system 106, engages a piston 112 within fluid reservoir, thereby transferring pressure from the working fluid to the drilling fluid to be tested. Pressure system 106 may include a pump 114, a pre-charged cylinder 116, or any other mechanism known to one of ordinary skill in the art to apply a pressure to the drilling fluid in reservoir 104. Furthermore, any acceptable gas or fluid may be used for the working fluid of pressure system, although one of ordinary skill will understand that an incompressible liquid may be preferred for the purpose of safety.

In one embodiment, pressure system 106 includes piston-driven hydraulic pump for pump 114 and a nitrogen-charged gas accumulator for pre-charged cylinder 116. As such nitrogen, a compressible gas, may be stored in cylinder 116 at high (e.g., 5,000 psi) and used to pressurize the working fluid of pressure system 106 through piston 118. Therefore, pre-charged cylinder 116 may supply the bulk of the pressure to piston 112 in fluid reservoir 104, with pump 114 used to either supply additional pressure, or to re-charge pre-charged cylinder 116 to a desired pressure. Pre-charged cylinder 116 is desirably included within pressure system 106 because it is capable of instantly supplying (and maintaining) a large amount of constant pressure upon demand. Pumps (e.g., 114) alone are typically not as capable of supplying such pressure upon demand. Nonetheless, in alternative embodiments, pump 114 may be capable of supplying all pressure to fluid reservoir 104 upon demand.

Referring still to FIG. 1, a test valve 120 is connected between inlet 108 of test housing 102 and fluid reservoir 104. A sample valve 122 is connected to outlet 110 at the distal end of test housing 102 and leads to a measurement device shown schematically at 124. Valves 120, 122 may be of any type known to those of skill in the art, but are preferably configured to allow unrestricted flow of fluids therethrough once opened. Measurement device 124 is configured to measure the amount of drilling fluid flowing from sample valve 122 and may be of any type and configuration known to those of skill in the art.

In one embodiment, measurement device 124 includes a fluid container (e.g., a beaker) positioned upon a scale, wherein the scale is configured to output the mass of filtrate fluid (i.e., a combination of drilling fluid and surrogate fluid as described below, if used) flowing through sample valve 122 to a computer where it is recorded as a function of elapsed time. In another embodiment, measurement device 124 may comprise a mass-flow meter configured to measure (and record) the mass of filtrate fluid flowing through sample valve 122 as a function of elapsed time. In yet another embodiment, measurement device 124 may comprise a volumetric flow meter configured to record the volume of filtrate fluid flowing through sample valve 122 as a function of elapsed time. One of ordinary skill in the art will appreciate that various other measurement sensors may be used by measurement device 124 to quantify the amount of filtrate fluid flowing through sample valve 122. Furthermore, in any embodiment, measurement device 124 may also include additional sensors (e.g., pressure transducers, thermometers, densitometers, etc.) to measure and record various characteristics of filtrate fluid passing through sample valve 122 as a function of elapsed time.

Further, test housing 102 includes a test matrix 126 for the drilling fluid within reservoir 104 to be tested with. Test matrix 126 may be any formation or simulated formation known to one of ordinary skill that the drilling fluid housed within reservoir 104 is to be tested with. In one embodiment, test matrix 126 may be constructed of a "sand pack" comprising particles (e.g., sand, ground-up rock, etc.) of a known granular size and density. In another embodiment, test matrix 126 may be constructed of a sand pack on top of a ceramic permeability disc of known pore size. For example, a 20/40 mesh (400-1000 micron) sand may be used in conjunction with a 90 micron ceramic permeability disc to construct test matrix 126. In yet another embodiment, test matrix 126 may include a core sample from an actual subterranean formation to be tested with the drilling fluid composition housed within reservoir 104. If a core sample is to be used for test matrix 126, the core sample may be encased in rubber (or any other fluid restrictive material) to prevent test fluid from radially escaping and bypassing a portion of test matrix 126. Alternatively still, test matrix 126 may comprise any sample, either granular or solid, known to approximate formation conditions expected to be experienced downhole.

In selected embodiments, test matrix 126 may be "pre-soaked" with a surrogate fluid prior to encountering the drilling fluid to be tested. Such surrogate fluids may include de-aerated water, low-toxicity mineral oil, or any other appropriate fluid known to one of ordinary skill in the art. As such, the surrogate fluid may be selected such that its density and flow characteristics are similar to the base of the drilling fluid composition to be tested. Alternatively, surrogate fluid may be selected to approximate a fluid of an expected downhole formation. Furthermore, surrogate fluid may be selected to be any fluid useful in testing the permeability of test matrix 126.

Before a test, test housing 102 may be disconnected from fluid reservoir 104 so that test matrix 126 may be pre-soaked. Accordingly, the surrogate fluid may be manually poured through test matrix 126 and allowed to flow out sample valve 122. With sample valve 122 closed, the level of the surrogate fluid may be adjusted to the top surface of test matrix 126 and reservoir 104 and test housing 102 reconnected. By opening test valve 120, pressure may be applied to the surrogate fluid and test matrix 126 for compaction.

Fluid reservoir 104 may contain a drilling fluid composition to be tested through test matrix 126. Thus, the drilling fluid composition may contain bridging solids or loss prevention materials expected to shorten or reduce the amount of fluid loss following spurt loss. With test valve 120 in the open position, the fluid reservoir 104 is filled with the drilling fluid composition to be tested. Test valve 120 may be left open in this manner to allow the drilling fluid to be tested to come into contact with test matrix 126 and the surrogate fluid before the start of the test. With test valve 120 closed, pressure may be applied to the top side of piston 112 by pressure assembly 106.

As such, the drilling fluid to be tested may be pushed through test matrix 126 under pressure exerted by pressure assembly 106 through piston 112. Alternatively, drilling fluid may be pushed through test matrix 126 under gravitational forces alone. Pressure assembly 106 is configured to exert a differential pressure upon drilling fluid within reservoir 104 and thrust it through test matrix 126 so that loss of fluid (recorded by measurement device 124) over time may be measured. In one embodiment, apparatus 100 is rated to 10,000 psi but performs routine measurements at up to 7,000 psi differential pressure. However, one of ordinary skill in the art should appreciate that various pressure (and temperature) test ranges for test apparatus 100 are possible without departing from the subject matter as claimed.

In a selected embodiment, to perform a measurement, pressure is applied to drilling fluid in fluid reservoir 104 by pressure system 106 until a desired differential pressure is reached in reservoir 104. Upon reaching desired differential pressure, test valve 120 and sample valve 122 may be simultaneously opened to allow the pressurized fluid within reservoir 104 to engage test matrix 126 suddenly. Alternatively, test valve 120 may be slowly opened (i.e., the pressure release therethrough regulated) first to allow pressure in test housing 102 and fluid reservoir 104 to equalize, after which sample valve 122 may be opened (with or without similar regulation). In the latter circumstance, a pressure balancing line 128 may supply a backing pressure to sample valve 122 to help offset the pressure exerted by pressure system 106 when valve 122 is closed. In yet another alternative, both sample valve 122 and test valve 120 may be opened first and pressure applied to fluid reservoir 104 by pressure system 106 to effectuate a "ramping-up" of differential pressure of drilling fluid upon test matrix 126. This allows the differential pressure across test matrix 126 to rise gradually.

As such, various downhole pressure conditions may be simulated with test apparatus 100 through the selective opening, closing, and activation of valves 120, 122 and pressure system 106. The various modes of operation allow the effect of differential pressure on external and internal filtercake formation and on the quality of the filtercake to be studied. Furthermore, the varied testing modes permit an investigation of the depth of penetration of fine solids entrained within the drilling fluid to be tested into pores of test matrix 126.

Further, test valve 120 and sample valve 122 may be remotely operated by a computer system or other mechanism. Thus, a single computer system may be capable of monitoring and controlling pressure system 106, test valve 120, sample valve 122, and measurement device 124. Such a computer system may relate the control and outputted data to elapsed time so that a drilling fluid may be optimized for a particular formation (i.e. test matrix 126). Those having ordinary skill in the art should appreciate that various alternatives to measurement device 124 are contemplated by the present disclosure. For example, measurement device 124 may include a data-logging mechanism built into a scale, such that a separate computer system is not necessary to record filtrate fluid mass as a function of elapsed time. In another embodiment, measurement device 124 may include a lab technician noting filtrate fluid mass to a log book at pre-determined time intervals.

The matrix loss characteristics of the fluid to be tested may be determined from the weight-time data logged by measurement device 124. While the tests may be carried out at ambient temperature, it should be understood that apparatus 100 may be easily adapted to operate at higher temperatures. In one embodiment, electric blankets may be applied to test housing 102 and fluid reservoir 104 to perform the test at an elevated temperature. In selected embodiments, test housing 102 and fluid reservoir 104 may be heated to a temperature in excess of 50° C., a temperature in excess of 100° C., or a temperature in excess of 200° C. In other selected embodiments, only one of the test housing 102 and the fluid reservoir 104 may be heated to an elevated temperature. In yet another embodiment, entire test apparatus 100 may be heated (e.g., in an autoclave, an oven, etc.) to an elevated temperature.

Matrix Permeability Measurements

In addition to matrix loss tests, permeability tests may be performed on test matrix 126 with apparatus 100 using a procedure similar to that disclosed above. In particular, measurements may be carried out to determine the permeability of either water-wet or oil-wet test matrix 126 to water or oil, wherein either water or oil is used in place of the drilling fluid in fluid reservoir 104. Such permeability measurements may be performed under gravitational flow or under external pressure, wherein the average value of permeability is calculated from the slope of a filtrate versus time profile and from the following equation:

$$K = \frac{qL\mu}{A\Delta P} \quad (\text{Eq. 1})$$

Where K is permeability in Darcy, q is volume flow rate in cm$^3$/s, L is the length of flow path in cm, $\mu$ is fluid viscosity in cP (equivalent to mPa·s), A is cross-sectional area of the porous medium in cm$^2$ and $\Delta P$ is differential pressure in atm. Permeability measured in this type of apparatus is an overall nominal value corresponding to the combination of the test matrix 126 (i.e., the sand pack and ceramic disc) and the geometry of the contraction in an end plate of test housing 102 (i.e., the discharge hole), sample valve 122, etc.

The following examples illustrate the use of the apparatus for determination of matrix permeability and matrix loss characteristics of drilling fluids.

Determination of Matrix Permeability

Figure 2:
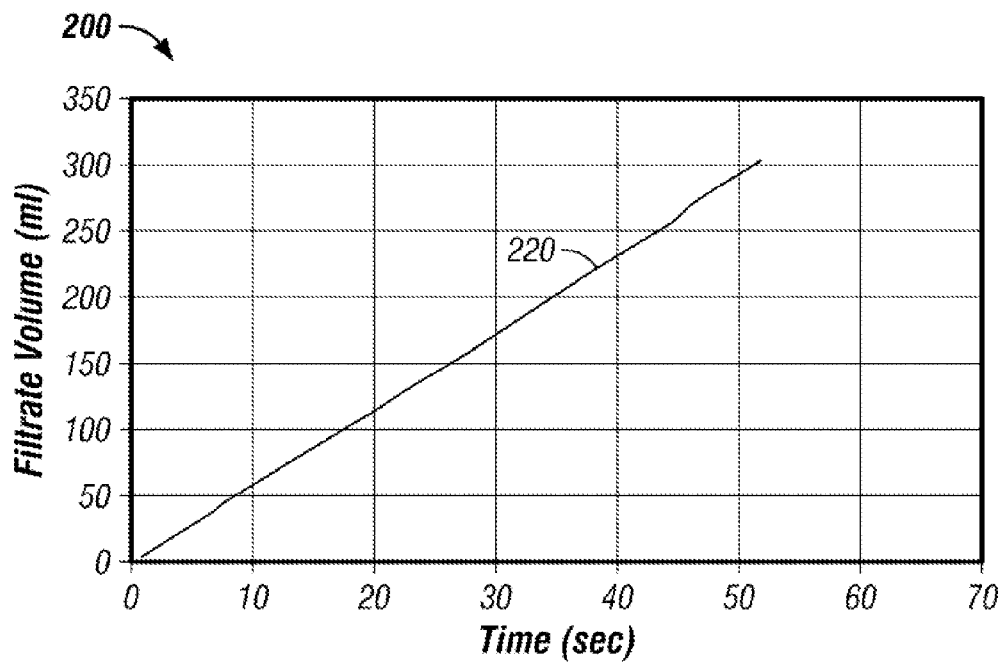
FIG. 2 is a graphical representation of a flow profile of a fluid through a sand pack in accordance with embodiments of the present disclosure.

Referring now to FIG. 2, the permeability of a water-wet, 20/40-mesh sand pack test matrix (e.g., 126 of FIG. 1) to water was measured under gravitational flow of a column of de-aerated water with a constant hydrostatic head of 37.5 cm, equivalent to 0.53 psi. FIG. 2 shows a flow profile 200 for the flow of water through the water-wet sand pack test matrix. The flow rate q was determined from slope of filtrate volume-time line 220 and the permeability of the water-wet sand pack to water was found to be 96.0 Darcy.

Effect of Loss Prevention Material on Matrix Loss

Figure 3:
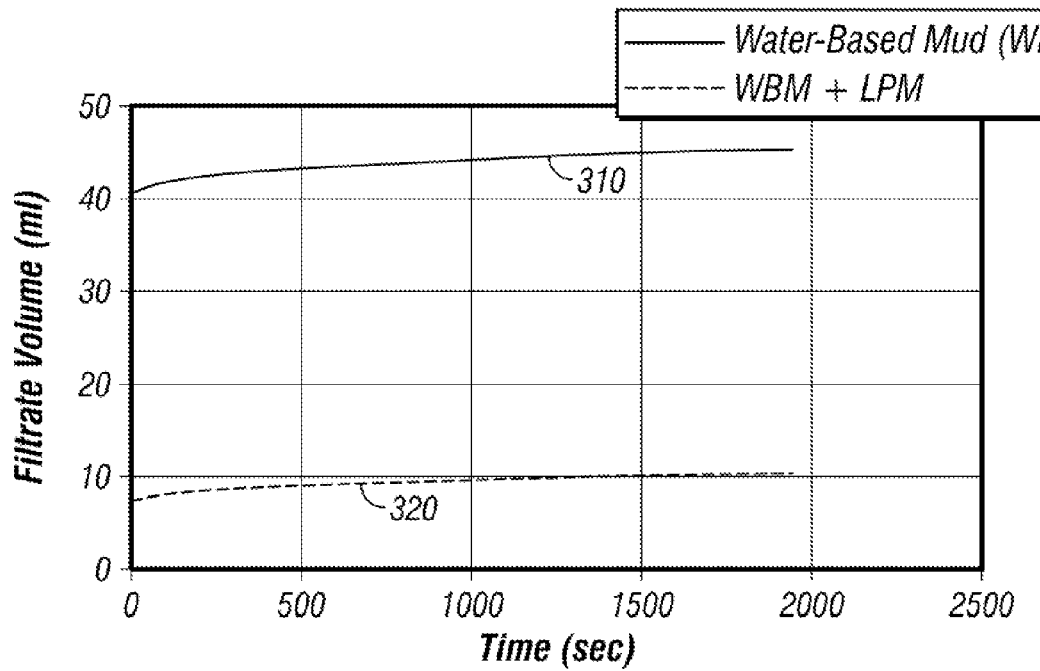
FIG. 3 is a graphical representation of matrix loss of drilling fluids through a sand pack in accordance with embodiments of the present disclosure.

Referring now to FIG. 3, the matrix loss of a bentonite water-based mud (curve 310) is compared with that of the same mud containing 40 pounds per barrel of an LPM consisting of sized carbonates and cellulosic materials (curve 320). The test matrix used for the test consisted of a 20/40-mesh sand pack and 500 psi of differential pressure was applied. The results show that the loss prevention material has a significant effect on reducing the spurt loss (i.e. fluid loss on first exposure to the matrix) of the fluid. The profiles 310, 320 also show that the loss rate decreases rapidly through the formation of an internal cake or gelling of the fluid in the pores of the test matrix. Furthermore, it should be understood that additional tests at varying concentrations, sizes and types of LPM may be performed to collect additional data. One of ordinary skill in the art would appreciate that such data would be useful in selecting an optimized LPM for a particular formation to be drilled.

Effect of Differential Pressure on Matrix Loss

Figure 4:
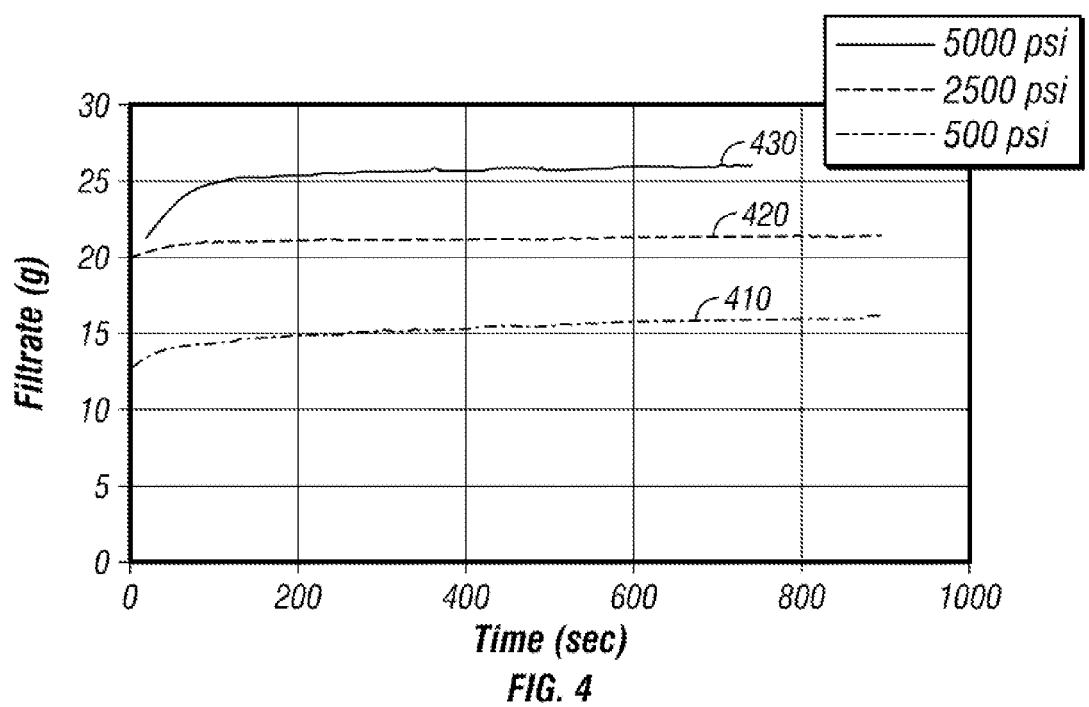
FIG. 4 is a graphical representation of matrix loss of a drilling fluid through a sand pack at varying pressures in accordance with embodiments of the present disclosure.

Referring now to FIG. 4, the matrix loss of an oil-based drilling fluid, containing 40 pounds per barrel of carbonates and graphitic material as LPM, was measured at varying differential pressures. The test matrix used was a 20/40-mesh sand pack saturated with a mineral oil and was tested at 500 psi (curve 410), 2500 psi (curve 420), and 5000 psi (curve 430). As shown in FIG. 4, spurt loss increases with increasing differential pressure. Furthermore, it should be understood that additional tests at varying temperatures may be performed to collect additional data. As such, one of ordinary skill in the art would appreciate that such data would be useful in selecting an optimized LPM for a particular formation to be drilled. Furthermore, if an optimized drilling fluid/LPM composition is found through data like that described in reference to FIG. 3, tests as described in accordance to FIG. 4 may be used to further evaluate the performance of such "optimized" fluid at temperatures and pressured expected to be experienced downhole. If the performance of the optimized fluid a temperature and pressure is less than desired, additional formulation changes may be performed to further optimize the drilling fluid/LPM composition.

Advantageously, methods and apparatus described herein relate to investigative techniques for evaluating the matrix loss characteristics of drilling fluids when drilling through either high-permeability formations or through formations containing natural or induced fractures. The techniques disclosed herein enable the optimization of the LPM, as well as base mud rheology, thereby preventing severe mud losses and reducing risks associated with such formations including, but not limited to, as differential sticking and formation damage.

We claim:

1. An apparatus to measure flow of a drilling fluid composition, the apparatus comprising:
   a test housing comprising a test matrix located between an inlet and an outlet;
   a test valve connected between the inlet of the test housing and a fluid reservoir;
   a pressure assembly configured to apply pressure to drilling fluid contained in the fluid reservoir;
   a sample valve connected to the outlet of the test housing; and
   a measurement device configured to measure a filtrate fluid flowing through the outlet.

2. The apparatus of claim 1, wherein the test matrix comprises a core sample.

3. The apparatus of claim 1, wherein the measurement device is configured to measure and record filtrate fluid flowing through the outlet as a function of time.

4. The apparatus of claim 1, wherein the measurement device is configured to measure matrix loss of the drilling fluid.

5. The apparatus of claim 1, wherein the measurement device is configured to measure permeability of the test matrix.

6. The apparatus of claim 1, wherein the sample valve further comprises a back pressure source.

7. The apparatus of claim 1, wherein the test matrix comprises a sand pack.

8. The apparatus of claim 7, wherein the test matrix comprises a ceramic permeability plate.

9. The apparatus of claim 1, wherein the fluid reservoir comprises a known volume of the drilling fluid.

10. The apparatus of claim 9, wherein the pressure assembly comprises a pre-charge cylinder.

11. The apparatus of claim 9, wherein the pressure assembly comprises a piston pump.

12. A method to measure flow of a drilling fluid, the method comprising:
    locating a test matrix in a test housing, the test housing comprising an inlet in communication with a test valve and an outlet in communication with a sample valve;
    selectively communicating a fluid reservoir with the test housing through the test valve;
    pressurizing drilling fluid in the fluid reservoir with a pressure assembly;
    opening the sample valve;
    opening the test valve; and
    measuring an amount of filtrate fluid flowing through the test matrix as a function of time.

13. The method of claim 12, further comprising soaking the test matrix with the drilling fluid prior to measuring the amount of filtrate fluid flowing through the test matrix.

14. The method of claim 12, wherein the pressure assembly comprises a pre-charge cylinder.

15. The method of claim 12, wherein the pressure assembly comprises a piston pump.

16. The method of claim 12, further comprising applying back pressure to the sample valve when in a closed position.

17. The method of claim 12, further comprising opening the test valve before opening the sample valve.

18. The method of claim 12, further comprising opening the sample and test valves at the same time.

19. The method of claim 12, further comprising opening the sample and test valves before pressurizing the drilling fluid with the pressure assembly.

20. The method of claim 12, further comprising determining the permeability of the test matrix.

21. The method of claim 12, further comprising soaking the test matrix with a surrogate fluid prior to measuring the amount of filtrate fluid flowing through the test matrix.

22. The method of claim 21, wherein the surrogate fluid comprises a fluid selected from at least one of mineral or synthetic oil.

23. The method of claim 21, wherein the surrogate fluid comprises at least one aqueous liquid selected from water or brine.

24. The method of claim 12, further comprising determining an effectiveness of a loss prevention material entrained within the drilling fluid on the test matrix.

25. The method of claim 24, wherein the effectiveness is determined by the amount of filtrate fluid measured as a function of time.

* * * * *